United States Patent
Ye et al.

(10) Patent No.: US 11,529,226 B2
(45) Date of Patent: Dec. 20, 2022

(54) ARTIFICIAL SKIN AND A PREPARATION METHOD THEREOF

(71) Applicant: CENTRAL MEDICAL (HUBEI) CO., LTD., Ezhou (CN)

(72) Inventors: Hongchuan Ye, Ezhou (CN); Xiong Zhou, Ezhou (CN); Hanmin Hu, Ezhou (CN)

(73) Assignee: CENTRAL MEDICAL (HUBEI) CO., LTD., Ezhou (CN)

( * ) Notice: Subject to any disclaimer, the term of this patent is extended or adjusted under 35 U.S.C. 154(b) by 934 days.

(21) Appl. No.: 16/355,249

(22) Filed: Mar. 15, 2019

(65) Prior Publication Data

US 2020/0229915 A1    Jul. 23, 2020

(30) Foreign Application Priority Data

Jan. 11, 2019  (CN) .......................... 201910026843.1

(51) Int. Cl.
| | |
|---|---|
| *B33Y 10/00* | (2015.01) |
| *A61L 24/00* | (2006.01) |
| *A61F 2/10* | (2006.01) |
| *A61L 27/44* | (2006.01) |
| *A61L 27/60* | (2006.01) |
| *B33Y 80/00* | (2015.01) |

(52) U.S. Cl.
CPC .............. *A61F 2/105* (2013.01); *A61L 27/44* (2013.01); *A61L 27/60* (2013.01); *A61L 2300/102* (2013.01); *A61L 2300/236* (2013.01); *A61L 2430/40* (2013.01); *B33Y 10/00* (2014.12); *B33Y 80/00* (2014.12)

(58) Field of Classification Search
CPC ................................... A61F 2/105; A61F 2/10
See application file for complete search history.

(56) References Cited

U.S. PATENT DOCUMENTS

| | | | | |
|---|---|---|---|---|
| 2004/0018149 A1* | 1/2004 | Noll | ......................... | A61L 27/60 424/9.1 |
| 2005/0186286 A1* | 8/2005 | Takami | ................... | A61K 35/36 435/68.1 |
| 2006/0135921 A1* | 6/2006 | Wiercinski | ............. | A61Q 19/00 604/368 |
| 2007/0269791 A1* | 11/2007 | Takami | .................... | A61L 27/60 435/1.1 |
| 2008/0195229 A1* | 8/2008 | Quijano | ............... | A61L 27/3604 623/23.72 |
| 2010/0196870 A1* | 8/2010 | Stone | ...................... | A61K 35/34 435/1.1 |
| 2011/0052693 A1* | 3/2011 | Kao | ........................ | A61P 17/02 435/373 |
| 2018/0105781 A1* | 4/2018 | Ou | .......................... | C12M 21/08 |

FOREIGN PATENT DOCUMENTS

| | | | | |
|---|---|---|---|---|
| CN | 105885436 A | * | 8/2016 | ......... A61L 27/3633 |
| CN | 104068945 B | * | 11/2016 | |

OTHER PUBLICATIONS

Yang et al. Assessment of the characteristics and biocompatibility of gelatin sponge scaffolds prepared by various crosslinking methods. Scientific Reports (2018) 8:1616 pp. 1-13 (Year: 2018).*
Hu et al. Synergistic effect of carbodiimide and dehydrothermal crosslinking on acellular dermal matrix. International Journal of Biological Macromolecules 55 (2013) 221-230 (Year: 2013).*
Zhao et al. Influence of hyaluronic acid on wound healing using composite porcine acellular dermal matrix grafts and autologous skin in rabbits. International Would Journal. 2012 (Year: 2012).*
Ma et al. Thermal dehydration treatment and glutaraldehyde crosslinking to increase the biostability of collagen chitosan porous scaffolds used as dermal equivalent. J Biomater Sci Polym Ed. 2003;14(8):861-74. (Year: 2003).*

* cited by examiner

*Primary Examiner* — Cachet I Proctor
(74) *Attorney, Agent, or Firm* — Platinum Intellectual Property LLP

(57) ABSTRACT

The present invention provides an artificial skin and a preparation method thereof. The present invention takes the xenogeneic acellular dermal matrix particles as main materials, and obtains the dermis layer by three-dimensional printing technologies, and then obtains the artificial skin by combining the epidermis layer with the dermis layer. The dermis layer of artificial skin in present invention has three-dimensional porous structure, which retains main components of natural dermal matrix in composition, and imitates distributed structure at fiber bundle diameter and pore size of natural dermal matrix in structure. This kind of novel biomimetic dermal scaffolds have obvious advantages in inducing migration and regeneration of skin cells, accelerating vascularization, promoting wound healing and improving healing quality. The dermis layer of artificial skin in present invention is obtained by three-dimensional printing technologies, which has precise and controllable structure, simple preparation method and high products qualification rate.

5 Claims, No Drawings

ARTIFICIAL SKIN AND A PREPARATION METHOD THEREOF

RELATED APPLICATIONS

This application is a Non-provisional Application under 35 USC 111(a), which claims priority of Chinese Patent Application No. 201910026843.1, filed Jan. 11, 2019, the disclosure of all of which are hereby incorporated by reference in their entirety.

TECHNICAL FIELD

The present invention belongs to the field of biomedical materials, and particularly relates to an artificial skin and a preparation method thereof.

BACKGROUND OF THE INVENTION

As the largest organ in human body, the skin has the functions of body fluid loss protection, biological barrier and the like. The treatment of large-area skin defects caused by burns, scald, trauma and ulcers is a major clinical problem, and surgical implantation of skin substitutes, the main used treatment, can accelerate the healing rate. However, autologous, allogeneic and xenogeneic (such as pigs, cattle, etc.) skin transplantation have the deficiency of limited source, immune rejection and easily transmitted diseases and the like; the xenogeneic acellular dermal matrix have the advantages of low immunogenicity, but its clinical effect is affected because of the destruction of its basement membrane and its insufficient adhesion to the wound surface; the commercial artificial skin, such as Integra, PELNAC and LANDO and the like, imitate the dermal structure of skin to a certain extent and show better clinical effect, but there are still many challenges in terms of wound healing quality such as reducing scar formation and promoting skin adnexal regeneration due to its insufficient imitation of component and structures. Therefore, it is of great significance to develop an artificial skin that can promote wound healing and improve healing quality.

Human natural skin histological studies have shown that the collagen in the natural dermal matrix is bundled, and the collagen bundles are interwoven to form a three-dimensional network structure and extend in all directions on the same horizontal surface, which is beneficial to vascularization and autologous cell growth. At the same time, the three-dimensional network shows a regular distribution on bundle diameter and pore size, that is, the upper (near epidermis) collagen bundle has a small diameter, and the three-dimensional network has a small pore size; the lower collagen bundle has a large diameter, and the three-dimensional network has a larger pore size. This provides a structural basis for the bionics of artificial dermal stents.

Fetal scarless healing studies have confirmed that, in the fetal dermal matrix, the collagen bundle diameter and the pore size between the collagen bundle is small, and the structure of collagen scaffold is similar to the surrounding normal tissue after wound healing, thereby achieving scar-free healing; however, in the adult dermal matrix, collagen bundle diameter and the pore size between the collagen bundle is larger, while the structure of collagen scaffold disappears and collagen bundles arranges perpendicular to the wound surface after the wound is healed, thereby resulting in scar formation. It can be seen that the regular distribution of three-dimensional network in the dermal matrix is essential for scarless healing. At the same time, hyaluronic acid content remained at a high level during fetal scar-free healing process, while hyaluronic acid levels decreased in abnormal scars, indicating that hyaluronic acid levels also affect scarless healing.

The present artificial dermal scaffolds face many challenges in preparation method, spatial structure, and clinical effect. In preparation method, freeze-drying is the main method in traditional technologies, though with simple process, the utilization rate of materials and the qualification rate of the products are low, and it is difficult to prepare complicated structure closed to the natural dermal scaffold. In spatial structure, present artificial dermal scaffolds only roughly imitate the three-dimensional reticular structure of natural dermal matrix which mostly only have a single structure, and the rare biomimetic structure is limited by the freeze-drying technology, besides, the biomimetic degree of structure is also very limited. In clinical effect, the dense scaffolds have good anti-scarring effect, but limit the migration rate of fibroblasts and thus result in slow vascularization rate; while the loose scaffolds are beneficial to the rapid entrance of blood vessels and cells, but show poor anti-scarring effect.

The three-dimensional printing technologies can realize fine-grained forming and can be used to prepare scaffolds with specific structure, size and thickness, and both pore size and degradation rate of three-dimensional-printed scaffolds can be controlled by adjusting the diameter of printing nozzle and the distance of printing. The xenogeneic acellular dermal matrix have the advantages of low immunogenicity, retaining main active components in the dermal matrix, and good biocompatibility. In addition, the particulate xenogeneic acellular dermal matrix is conducive to preparing gel, which can be highly matched with 3D printing technologies for the preparation of dermal scaffolds.

SUMMARY OF THE INVENTION

In view of this, the present invention provides an artificial skin and a preparation method thereof. The present invention takes the xenogeneic acellular dermal matrix particles as main materials, and obtains the dermis layer by three-dimensional printing technologies, and then obtains the artificial skin by combining the epidermis layer with the dermis layer.

The first aspect of the present invention provides a preparation method of the artificial skin, comprising the following steps:

S1. preparing a xenogeneic acellular dermal matrix particles solution, transferring the solution into the printing syringe, vacuumizing to remove bubbles, and assembling to obtain a xenogeneic acellular dermal matrix gel;

S2. constructing three-dimensional model of dermis layer, setting printing parameters, and printing xenogeneic acellular dermal matrix gel obtained in S1, and then treating the printed products with processes of alcohol soaking, freeze-drying, glutaraldehyde vapor crosslinking, thermal crosslinking, and glutaraldehyde removing to obtain the dermis layer;

S3. combining dermis layer obtained in S2 with the epidermis layer to obtain the artificial skin.

Preferably, in step S1, the materials of the xenogeneic acellular dermal matrix gel comprises the xenogeneic acellular dermal matrix particles and a solvent; the particle size of the xenogeneic acellular dermal matrix particles is 10~400 μm, the concentration of the xenogeneic acellular dermal matrix particles is 10~30% as a mass percentage of the xenogeneic acellular dermal matrix gel; and the solvent is one or more of acetic acid aqueous solution, phosphate buffer solution and hexafluoroisopropanol.

Preferably, in step S1, the materials of xenogeneic acellular dermal matrix gel also comprises hyaluronic acid, and the concentration of the hyaluronic acid is 0.1~2% as a mass percentage of the xenogeneic acellular dermal matrix gel.

The xenogeneic acellular dermal matrix gel provided in the present invention is composed of a solute and a solvent, the solute can be a single xenogeneic acellular dermal matrix or a mixture of a xenogeneic acellular dermal matrix and an auxiliary material. The present invention further attempts to prepare acellular dermal matrix bundles with hyaluronic acid as auxiliary material.

Preferably, in step S1, the assembling process is performed at a temperature of 0~37° C. and a humidity of 40%~80% for 12~48 h.

Preferably, in step S2, the dermis layer is a bilayer three-dimensional porous scaffold which comprise a lower layer contacted with wound surface and an upper layer combined with the epidermis layer, both lower and upper layer of the dermis layer are composed of fiber bundles obtained by printing xenogeneic acellular dermal matrix gel with two nozzles respectively.

Preferably, the printing parameters of the lower layer of dermis layer is: a fiber bundle diameter of 100~200 μm, a nozzle moving speed of 0.5~20 mm/s, a fiber bundle spacing distance of 100~200 μm, a printing pressure of 5~50 kPa, a printing platform temperature of −4~20° C., a thickness of 2000~4000 μm; and the printing parameter of the upper layer of dermis layer is: a fiber bundle diameter of 20~100 μm, a nozzle moving speed of 0.5~20 mm/s, a fiber bundle spacing distance of 20~100 μm, a printing pressure of 5~50 kPa, a printing platform temperature of −4~20° C., a thickness of 500~1000 μm.

Preferably, in step S2, the alcohol soaking process is performed in 10~20% (v/v) alcohol at 0~4° C. for 12~48 h; the glutaraldehyde vapor crosslinking process is performed in 10~30% glutaraldehyde vapor at 37~52° C. for 2~5 h, the thermal crosslinking process is performed in 10~150 Pa condition at 100~110° C. for 12~48 h; the glutaraldehyde removing process is performed at 37~52° C. for 2~5 d.

Preferably, in step S3, the epidermis layer is a medical microporous silicone membrane.

Preferably, in step S3, the medical microporous silicone membrane is combined with the upper layer of dermis layer by an adhesive, and the adhesive is preferably a biocompatible material such as α-amino acrylate, silicone rubber, polydimethylsiloxane, polyethylene terephthalate and the like.

The second aspect of the present invention provides an artificial skin, the dermis layer of the artificial skin have a similar distributed structure at fiber bundle diameter and pore size with the natural dermis layer of a human skin, which is obtained by the preparation method provided above.

Compared with the present technologies, the beneficial effects of the present invention are as follows:

1. The dermis layer of the artificial skin in the present invention takes the xenogeneic acellular dermal matrix particles as the main materials, which has the advantages of safety wide source, low immunogenicity, good biocompatibility, and is conducive to cell migration and regeneration. Meanwhile, particulate xenogeneic acellular dermal matrix is conducive to the preparation of printing gel, and thereby enhance the stability and qualification rate of the printed products.

2. Hyaluronic acid has good biocompatibility and the function of water retention, which is conducive to the preparation of printing gel. During the wound healing process, the hyaluronic acid is released along with the degradation of dermis scaffold, which can increase the concentration of hyaluronic acid around the wound, and thereby enhance the anti-scarring effect of the artificial skin.

3. The dermal layer of the artificial skin in the present invention has three-dimensional reticular structure, and is similar to the natural dermal matrix of human skin in fiber bundle diameter and pore size. The fiber bundle diameter and pore size of the lower layer of dermis layer is larger, which is conducive to the rapid migration and regeneration of fibroblast, accelerates vascularization and promotes wound healing. The fiber bundle diameter and pore size of the upper layer of dermis layer is smaller, which plays a good anti-scarring role in the later stage of wound healing.

4. The dermis layer of the artificial skin in the present invention is obtained by three-dimensional printing technologies, which has the advantages of precise controllable structure, simple preparation process and high product qualification rate. The processes designed for the treatment of printed products is conducive to enhancing the stability and maintaining the original structure of the printed products: the alcohol soaking process can enhance the crystallinity and facilitate the curing process of printed product, and play an anti-freezing effect in freeze-drying process to prevent printed products from being frozen to crack; the glutaraldehyde vapor crosslinking process is easy to perform, and can effectively prevent printed products from being frozen to damages, which usually caused by the present glutaraldehyde solution crosslinking process; the thermal crosslinking process has the effect of dehydration and sterilization, which is conducive to enhancing the stability of printed product. Meanwhile, the pore size, the mechanical properties and the degradation rate of the dermis layer can be controlled by adjusting the particle size and concentration of the xenogeneic acellular dermal matrix particle, the assembly process, the nozzle diameter, the fiber bundle spacing distance and the thickness of printing layer, thereby to meet the needs of different wound healing.

DETAILED DESCRIPTION OF THE INVENTION

For better understanding of the present invention, the present invention is described comprehensively and specifically below in connection with specific embodiments, but the scope of protection of the present invention is not limited to the following specific embodiments.

Unless otherwise defined, all technical terms used hereinafter have the same meaning as commonly understood by those skilled in the art. The terminologies used herein is only for the purpose of describing specific embodiments and is not intended to limit the scope of protection of the present invention.

Unless otherwise specified, various materials, reagents, instruments, equipment, and the like used in the present invention are commercially available or can be prepared by present methods.

Example 1

A preparation method of an artificial skin, comprising the following steps:

S1. Dissolving the porcine skin-derived acellular dermal matrix particles which have a particle size of 30~90 μm in 0.10 M acetic acid to prepare a 10% (w/w) solution, transferring the solution into printing syringe, vacuumizing to remove bubbles, and assembling at a temperature of 37° C. and a humidity of 40% for 12 h to obtain a xenogeneic acellular dermal matrix gel.

S2. Constructing three-dimensional model of dermis layer and setting the printing parameters. Specifically, the printing parameters of the lower layer of dermis layer is: a fiber bundle diameter of 100 μm, a syringe moving speed of 5~10 mm/s, a fiber space of 100×100×100 μm, a printing pressure of 5~15 kPa, a printing platform temperature of 0° C., a thickness of 3000 μm; the printing parameters of the upper layer of dermis layer is: a fiber bundle diameter of 20 μm, a nozzle moving speed of 5~10 mm/s, a fiber space of 40×40×40 μm, a printing pressure of 20~40 kPa, a printing platform temperature of 0° C., a thickness of 500 μm. Importing the above printing parameters into the printer and printing the gel obtained in S1 with two nozzles respectively, and then treating the printed products with the processes of alcohol soaking, freeze-drying, glutaraldehyde vapor crosslinking, thermal crosslinking, and glutaraldehyde removing to obtain the dermis layer. Specifically, the alcohol soaking process is performed in 10% (v/v) alcohol at 0° C. for 24 h; the glutaraldehyde vapor crosslinking process is performed with 10% glutaraldehyde vapor at 40° C. for 5 h, the thermal crosslinking process is performed in 100 Pa condition at 100° C. for 48 h; the glutaraldehyde removing process is performed at 37° C. for 2 d.

S3. Combining the medical microporous silicone membrane with the upper layer of dermis layer obtained in S2 with an adhesive to obtain the artificial skin. In this embodiment, the adhesive is polydimethylsiloxane.

Example 2

A preparation method of an artificial skin, comprising the following steps:

S1. Dissolving the porcine skin-derived acellular dermal matrix particles which have a particle size of 100~180 μm in 0.10 M acetic acid to prepare a 20% (w/w) solution, transferring the solution into printing syringe, vacuumizing to remove bubbles, and assembling at a temperature of 25° C. and a humidity of 60% for 24 h to obtain a xenogeneic acellular dermal matrix gel.

S2. Constructing three-dimensional model of dermis layer and setting the printing parameters. Specifically, the printing parameters of the lower layer of dermis layer is: a fiber bundle diameter of 120 μm, a syringe moving speed of 5~10 mm/s, a fiber space of 140×140×140 μm, a printing pressure of 5~15 kPa, a printing platform temperature of 4° C., a thickness of 2700 μm; the printing parameters of the upper layer of dermis layer is: a fiber bundle diameter of 40 μm, a nozzle moving speed of 5~10 mm/s, a fiber space of 60×60×60 μm, a printing pressure of 20~40 kPa, a printing platform temperature of 0° C., a thickness of 800 μm. Importing the above printing parameters into the printer and printing the gel obtained in S1 with two nozzles respectively, and then treating the printed products with the processes of alcohol soaking, freeze-drying, glutaraldehyde vapor crosslinking, thermal crosslinking, and glutaraldehyde removing to obtain the dermis layer. Specifically, the alcohol soaking process is performed in 15% (v/v) alcohol at 4° C. for 24 h; the glutaraldehyde vapor crosslinking process is performed with 20% glutaraldehyde vapor at 40° C. for 3 h, the thermal crosslinking process is performed in 100 Pa condition at 100° C. for 48 h; the glutaraldehyde removing process is performed at 37° C. for 2 d.

S3. Combining the medical microporous silicone membrane with the upper layer of dermis layer obtained in S2 with an adhesive to obtain the artificial skin. In this embodiment, the adhesive is silicone rubber.

Example 3

A preparation method of an artificial skin, comprising the following steps:

S1. Dissolving the porcine skin-derived acellular dermal matrix particles which have a particle size of 200~350 μm in 0.10 M acetic acid to prepare a 30% (w/w) solution, transferring the solution into printing syringe, vacuumizing to remove bubbles, and assembling at a temperature of 4° C. and a humidity of 80% for 48 h to obtain a xenogeneic acellular dermal matrix gel.

S2. Constructing three-dimensional model of dermis layer and setting the printing parameters. Specifically, the printing parameters of the lower layer of dermis layer is: a fiber bundle diameter of 150 μm, a syringe moving speed of 5~10 mm/s, a fiber space of 200×200×200 μm, a printing pressure of 5~15 kPa, a printing platform temperature of 4° C., a thickness of 2500 μm; the printing parameters of the upper layer of dermis layer is: a fiber bundle diameter of 60 μm, a nozzle moving speed of 5~10 mm/s, a fiber space of 80×80×80 μm, a printing pressure of 20~40 kPa, a printing platform temperature of 0° C., a thickness of 1000 μm. Importing the above printing parameters into the printer and printing the gel obtained in S1 with two nozzles respectively, and then treating the printed products with the processes of alcohol soaking, freeze-drying, glutaraldehyde vapor crosslinking, thermal crosslinking, and glutaraldehyde removing to obtain the dermis layer. Specifically, the alcohol soaking process is performed in 20% (v/v) alcohol at 4° C. for 24 h; the glutaraldehyde vapor crosslinking process is performed with 30% glutaraldehyde vapor at 40° C. for 2 h, the thermal crosslinking process is performed in 100 Pa condition at 105° C. for 24 h; the glutaraldehyde removing process is performed at 50° C. for 4 d.

S3. Combining the medical microporous silicone membrane with the upper layer of dermis layer obtained in S2 with an adhesive to obtain the artificial skin. In this embodiment, the adhesive is α-amino acrylate.

Example 4

A preparation method of an artificial skin, comprising the following steps:

S1. Dissolving the porcine skin-derived acellular dermal matrix particles which have a particle size of 100~180 μm in 0.10 M acetic acid to prepare a 20% (w/w) solution, dissolving the hyaluronic acid in 0.10 M acetic acid to prepare a 0.5% (w/w) solution, mixing the above two solution and performing uniform mechanical stirring transferring the solution into printing syringe, vacuumizing to remove bubbles, and assembling at a temperature of 25° C. and a humidity of 60% for 24 h to obtain a xenogeneic acellular dermal matrix gel.

S2. Constructing three-dimensional model of dermis layer and setting the printing parameters. Specifically, the printing parameters of the lower layer of dermis layer is: a fiber bundle diameter of 120 μm, a syringe moving speed of 5~10 mm/s, a fiber space of 140×140×140 μm, a printing pressure of 5~15 kPa, a printing platform temperature of 4° C., a thickness of 2700 μm; the printing parameters of the upper layer of dermis layer is: a fiber bundle diameter of 40 μm, a nozzle moving speed of 5~10 mm/s, a fiber space of 60×60×60 μm, a printing pressure of 20~40 kPa, a printing platform temperature of 0° C., a thickness of 800 μm. Importing the above printing parameters into the printer and printing the gel obtained in S1 with two nozzles respectively, and then treating the printed products with the processes of alcohol soaking, freeze-drying, glutaraldehyde vapor crosslinking, thermal crosslinking, and glutaraldehyde removing to obtain the dermis layer. Specifically, the alcohol soaking process is performed in 15% (v/v) alcohol at 4° C. for 24 h; the glutaraldehyde vapor crosslinking process is performed with 20% glutaraldehyde vapor at 40° C. for 3 h, the thermal crosslinking process is performed in 100 Pa condition at 105° C. for 24 h; the glutaraldehyde removing process is performed at 37° C. for 2 d.

S3. Combining the medical microporous silicone membrane with the upper layer of dermis layer obtained in S2 with an adhesive to obtain the artificial skin. In this embodiment, the adhesive is polydimethylsiloxane.

Example 5

A preparation method of an artificial skin, comprising the following steps:

S1. Dissolving the porcine skin-derived acellular dermal matrix particles which have a particle size of 100~180 μm in phosphate buffer solution to prepare a 20% (w/w) solution, transferring the solution into printing syringe, vacuumizing to remove bubbles, and assembling at a temperature of 4° C. and a humidity of 80% for 48 h to obtain a xenogeneic acellular dermal matrix gel.

S2. Constructing three-dimensional model of dermis layer and setting the printing parameters. Specifically, the printing parameters of the lower layer of dermis layer is: a fiber bundle diameter of 150 μm, a syringe moving speed of 5~10 mm/s, a fiber space of 200×200×200 μm, a printing pressure of 5~15 kPa, a printing platform temperature of 4° C., a thickness of 2500 μm; the printing parameters of the upper layer of dermis layer is: a fiber bundle diameter of 60 μm, a nozzle moving speed of 5~10 mm/s, a fiber space of 80×80×80 μm, a printing pressure of 20~40 kPa, a printing platform temperature of 0° C., a thickness of 1000 μm. Importing the above printing parameters into the printer and printing the gel obtained in S1 with two nozzles respectively, and then treating the printed products with the processes of alcohol soaking, freeze-drying, glutaraldehyde vapor crosslinking, thermal crosslinking, and glutaraldehyde removing to obtain the dermis layer. Specifically, the alcohol soaking process is performed in 20% (v/v) alcohol at 4° C. for 24 h; the glutaraldehyde vapor crosslinking process is performed with 30% glutaraldehyde vapor at 40° C. for 2 h, the thermal crosslinking process is performed in 100 Pa condition at 105° C. for 48 h; the glutaraldehyde removing process is performed at 50° C. for 4 d.

S3. Combining the medical microporous silicone membrane with the upper layer of dermis layer obtained in S2 with an adhesive to obtain the artificial skin. In this embodiment, the adhesive is polydimethylsiloxane.

Example 6

A preparation method of an artificial skin, comprising the following steps:

S1. Dissolving the porcine skin-derived acellular dermal matrix particles which have a particle size of 100~180 μm in hexafluoroisopropanol to prepare a 20% (w/w) solution, transferring the solution into printing syringe, vacuumizing to remove bubbles, and assembling at a temperature of 4° C. and a humidity of 80% for 48 h to obtain a xenogeneic acellular dermal matrix gel.

S2. Constructing three-dimensional model of dermis layer and setting the printing parameters. Specifically, the printing parameters of the lower layer of dermis layer is: a fiber bundle diameter of 150 μm, a syringe moving speed of 5~10 mm/s, a fiber space of 200×200×200 μm, a printing pressure of 5~15 kPa, a printing platform temperature of 4° C., a thickness of 2500 μm; the printing parameters of the upper layer of dermis layer is: a fiber bundle diameter of 60 μm, a nozzle moving speed of 5~10 mm/s, a fiber space of 80×80×80 μm, a printing pressure of 20~40 kPa, a printing platform temperature of 0° C., a thickness of 1000 μm. Importing the above printing parameters into the printer and printing the gel obtained in S1 with two nozzles respectively, and then treating the printed products with the processes of alcohol soaking, freeze-drying, glutaraldehyde vapor crosslinking, thermal crosslinking, and glutaraldehyde removing to obtain the dermis layer. Specifically, the alcohol soaking process is performed in 20% (v/v) alcohol at 4° C. for 24 h; the glutaraldehyde vapor crosslinking process is performed with 30% glutaraldehyde vapor at 40° C. for 2 h, the thermal crosslinking process is performed in 100 Pa condition at 105° C. for 48 h; the glutaraldehyde removing process is performed at 50° C. for 4 d.

S3. Combining the medical microporous silicone membrane with the upper layer of dermis layer obtained in S2 with an adhesive to obtain the artificial skin. In this embodiment, the adhesive is polydimethylsiloxane.

In the preparation method of the artificial skin provided in above-mentioned embodiments, the technology to obtain three-dimensional printing materials with xenogeneic acellular dermal matrix particles directly affects the three-dimensional printing process of the bilayer three-dimensional porous scaffolds and its spatial structure in the present invention, the concentration of solute, the selection of solvent and the conditions of assembly affects among each other, which together determine the properties of xenogeneic acellular dermal matrix gel and the morphology, structure and properties of the bilayer three-dimensional porous scaffolds. Furthermore, the processes particularly designed for the treatment of initial bilayer three-dimensional porous scaffolds product according to its characteristics directly affects the formation, stability of its spatial structure, and directly affects the effects including promoting wound healing and anti-scarring of final bilayer three-dimensional porous scaffolds product. After treated with these particularly designed processes, the ability to resist enzymatic hydrolysis, the stability and the qualified rate of final product can be enhanced.

The dermis layer in above-mentioned embodiment is obtained by three-dimensional printing technologies, which has the advantages of precise controllable structure, simple preparation process and high product qualification rate. The dermis layer of artificial skin in the present invention has three-dimensional porous structure, which retains the main components of the natural dermal matrix in composition, and simulates the distribution structure of the natural dermal matrix among fiber bundle diameter and pore size in structure. This kind of novel biomimetic dermal scaffold has obvious advantages in inducing migration and regeneration of skin cells, accelerating vascularization, promoting wound healing and improving the quality of healing.

Although the preferred embodiments of the present invention have been described, once the technicians in the field have learned about basic creative concepts, additional changes and modifications would be made to these embodiments. Therefore, the appended claims are intended to be interpreted as including the preferred embodiments and all changes and modifications falling within the protection scope of the present invention.

Obviously, technicians in this field can make various changes and variations to the present invention without departing from the spirit and protection scope of the invention. Thus, if these modifications and variations of the present invention fall within the scope of the claims of the present invention and their equivalent technologies, the present invention is also intended to include these modifications and variations.

The invention claimed is:

1. A preparation method for artificial skin, comprising the following steps:
   S1. preparing a xenogeneic acellular dermal matrix particles solution, transferring the solution into a printing syringe, vacuuming to remove bubbles, and assembling to obtain a xenogeneic acellular dermal matrix gel, wherein the xenogeneic acellular dermal matrix gel comprises the xenogeneic acellular dermal matrix particles, hyaluronic acid, and a solvent; the particle size of the xenogeneic acellular dermal matrix particles is 10-400 μm, and the concentration of the xenogeneic acellular dermal matrix particles is 10-30% as a mass percentage of the xenogeneic acellular dermal matrix gel; the concentration of the hyaluronic acid is 0.1-2% as a mass percentage of the xenogeneic acellular dermal matrix gel; the assembling process is performed at a temperature of 0-37° C. and a humidity of 40%-80% for 12-48 h;
   S2. constructing three-dimensional model of dermis layer, setting printing parameters, and printing xenogeneic acellular dermal matrix gel obtained in S1, and then treating the printed products with processes of alcohol soaking, freeze-drying, glutaraldehyde vapor crosslinking, thermal crosslinking, and glutaraldehyde removal to obtain the dermis layer, wherein the alcohol soaking process is performed in 10-20% (v/v) alcohol at 0-4° C. for 12-48 h; the glutaraldehyde vapor crosslinking process is performed in 10-30% glutaraldehyde vapor at 37-52° C. for 2-5 h, the thermal crosslinking process is performed in 10-150 Pa condition at 100-110 ° C. for 12-48 h; the glutaraldehyde removing process is performed at 37-52° C. for 2-5 d; and
   S3. combining dermis layer obtained in S2 with an epidermis layer to obtain the artificial skin.

2. The preparation method of the artificial skin according to claim 1, wherein the solvent is one or more of acetic acid aqueous solution, phosphate buffer solution and hexafluoroisopropanol.

3. The preparation method of the artificial skin according to claim 1, wherein in step S2, the dermis layer is a bilayer three-dimensional porous scaffold which comprise a lower layer contacting a wound surface and an upper layer combined with the epidermis layer, both lower and upper layer of the dermis layer are composed of fiber bundles obtained by printing the xenogeneic acellular dermal matrix gel with two nozzles respectively.

4. The preparation method of the artificial skin according to claim 3, wherein, the printing parameters of the lower layer of dermis layer is: a fiber bundle diameter of 100-200 m, a nozzle moving speed of 0.5-20 mm/s, a fiber bundle spacing distance of 100-200 m, a printing pressure of 5-50 kPa, a printing platform temperature of −4-20 C, a thickness of 2000-4000 m; and the printing parameter of the upper layer of dermis layer is: a fiber bundle diameter of 20-100 m, a nozzle moving speed of 0.5-20 mm/s, a fiber bundle spacing distance of 20-100 m, a printing pressure of 5-50 kPa, a printing platform temperature of −4-20 C, and a thickness of 500-1000 m.

5. The preparation method of the artificial skin according to claim 1, wherein in step S3, the epidermis layer is a medical microporous silicone membrane.

* * * * *